United States Patent [19]
Loos

[11] Patent Number: 5,935,054
[45] Date of Patent: Aug. 10, 1999

[54] MAGNETIC EXCITATION OF SENSORY RESONANCES

[76] Inventor: Hendricus G. Loos, 3019 Cresta Way, Laguna Beach, Calif. 92651

[21] Appl. No.: 08/486,918

[22] Filed: Jun. 7, 1995

[51] Int. Cl.⁶ ...................................................... A61N 2/00
[52] U.S. Cl. ............................................................ 600/9
[58] Field of Search ........................................... 600/9–15

[56] References Cited

U.S. PATENT DOCUMENTS

| | | | |
|---|---|---|---|
| 3,678,337 | 7/1972 | Grauvogel | 317/4 |
| 4,197,851 | 4/1980 | Fellus | 128/422 |
| 4,611,599 | 9/1986 | Bentall | 128/422 |
| 4,727,857 | 3/1988 | Horl | 600/15 |
| 5,667,469 | 9/1997 | Zhang et al. | 600/9 |

OTHER PUBLICATIONS

P. Lindemann, The Megabrain Report, vol. 1, #2, pp. 34–35 (1990).
P. Limdemann, The Megabrain Report, vol. 1, #1, pp. 30–31 (1990).

*Primary Examiner*—John P. Lacyk

[57] ABSTRACT

The invention pertains to influencing the nervous system of a subject by a weak externally applied magnetic field with a frequency near ½ Hz. In a range of amplitudes, such fields can excite the ½ sensory resonance, which is the physiological effect involved in "rocking the baby". The wave form of the stimulating magnetic field is restricted by conditions on the spectral power density, imposed in order to avoid irritating the brain and the risk of kindling. The method and apparatus can be used by the general public as an aid to relaxation, sleep, or arousal, and clinically for the control of tremors, seizures, and emotional disorders.

8 Claims, 4 Drawing Sheets

MAGNETIC EXCITATION OF SENSORY RESONANCES

BACKGROUND OF THE INVENTION

The human nervous system exhibits a sensitivity to certain low-frequency stimuli, as is evident from rocking a baby or relaxing in a rocking chair. In both cases, the maximum soothing effect is obtained for a periodic motion with a frequency near ½ Hz. The effect is here called "the ½ Hz sensory resonance". In the rocking response, the sensory resonance is excited principally by frequency-coded signals from the vestibular organ. However, the rocking motion also induces body strains, and these are detected by stretch receptors such as Ruffini corpuscules in the skin and muscle spindles throughout the body. In addition, signals may come from cutaneous cold and warmth receptors which report skin temperature variations caused by relative air currents induced by the rocking motion. All these receptors employ frequency coding in their sensory function, and it is believed that their signals are combined and compared with the vestibular nerve signals in an assessment of the somatic state. One may thus expect that the resonance can be excited separately not only through the vestibular nerve, but also through the other sensory modalities mentioned. This notion is supported by the observation that gently stroking of a child with a frequency near ½ Hz has a soothing effect as well. Appropriate separate stimulation of the other frequency-coding sensory receptors mentioned is expected to have a similar effect.

The notion has occurred that frequency-coding sensory receptors may perhaps respond to certain artificial stimulations, and that such stimulations could be used to cause excitation of the ½ Hz sensory resonance. This indeed can been done, by using externally applied weak electric fields as the artificial stimulus, as discussed in the U.S. patent application Ser. 08/447,394 [1]. Autonomic effects of this stimulation have been observed in the form of relaxation, drowsiness, sexual excitement, or tonic smile, depending on the precise electric field frequency near ½ Hz used. The question whether the effects are perhaps due to the direct action of the electric field on the brain has been settled by experiments in which localized weak electric fields are applied to areas of the skin away from the head; these experiments showed the same array of autonomic effects. It follows that the electric field acts on certain somatosensory nerves.

A major application of the electric exitation of the resonance is seen in the form of a sleeping aid. The method can further be used by the general public as an aid to relaxation and arousal, and clinically for the control of tremmors and seizures as well as disorders resulting from malfunctions of the autonomic nervous system, such as panic attacks.

Electric fields are subject to polarization effects that bar certain applications. These limitations would be circumvented if the excitation could be done by magnetic rather than electric fields. It is an object of the present invention to provide a method and apparatus for excitation of the ½ Hz sensory resonance by oscillatory magnetic fields.

An electromagnetic field apparatus for environmental control is discussed by Grauvogel in U.S. Pat. No. 3,678, 337. The apparatus is to re-create indoors the electric and magnetic fields that occur naturally out-of-doors, in the interest of physical and mental well-being. In advancing this notion, Grauvogel overlooks the fact that the earth's magnetic field is not shielded by buildings; therefore, the magnetic part of his apparatus is superfluous in the context of his objective. In Grauvogel's claims, the field of use is stated as "environmental control apparatus".

In U.S. Pat. No. 4,197,851 Fellus shows an apparatus for emitting high-frequency electromagnetic waves with a low intensity such as to avoid significant thermal effects in exposed tissue, employing an "antenna" which is applied closely to the skin via insulation material, in such a manner as to conform to body contours. Bentall, in U.S. Pat. No. 4,611,599 shows an electrical apparatus for influencing a metabolic growth characteristic, wherein a radio frequency electromagnetic field is applied to a subject at a low power level such as not to produce bulk heating of the exposed tissue. The high-frequencies used by Fellus and by Bentall are not suitable for exciting the ½ Hz sensory resonance.

A device for influencing subjects by means of pulsed electromagnetic fields has been discussed by Lindemann [2]. His "Centron" device comprises a square wave generator connected to an equiangular spiral coil with two branches. The pulse rate can be chosen from 12 discrete frequencies ranging from 1 to 18 Hz. Comments on the workings of the spiral coil are given by Lindeman [3] in the context of "scalar fields", a notion that happens to be in conflict with modern physics. According to Lindeman [3], the spiral coil of the Centron involves "a high degree of interaction between the inductance and capacitance, creating what is called a scalar". In spite of the erroneous physical basis presented, the Centron device may indeed affect the nervous system. However, several shortcomings are apparent in the design. First, the spiral coil is woefully inefficient and is therefore wasteful of electric current, a precious commodity in battery-operated devices. It may perhaps be thought that the spiral coil design provides localization of the magnetic field by clever cancellations, but that is not the case; a calculation of the steady asymptotic magnetic field induced by the coil shows that the far field is dominated by a dipole. Second, the frequency range of the device misses the ½ Hz sensory resonance alltogether, and the use of preset discrete frequencies hampers exploration of other resonances. Last but not least, the fundamental frequencies and some of the higher harmonics in the square wave produce nuisance signals in the brain, and pose a risk of kindling [4] in subjects with a disposition to epilepsy.

It is an object of the present invention to provide an efficient battery-powered device for inducing magnetic fields for the excitation of the ½ Hz sensory resonance without causing irritation to the brain or posing a threat of kindling.

Other devices that emit "scalar" fields for unspecified therapeutic purposes are the Teslar watch and the MicroHarmonizer, distributed by Tools For Exploration in San Rafael, Calif. The Teslar watch emits a pulsed magnetic field at a fixed frequency of 7.83 Hertz, and the MicroHarmonizer can be switched to either 7.83 Hz or 3.91 Hz. Neither device can be tuned to the ½ Hz sensory resonance.

There is much public concern about the health effects of low-frequency electromagnetic fields. In response, governments have issued guide lines for manufacturers of electronic equipment. Among these, the Swedish MPRII guide lines are the strictest in the world. For human exposure to low-frequency magnetic fields, MPRII calls for an upper limit of 250 nT in the frequency band from 5 Hz to 2 KHz, and 25 nT in the band from 2 KHz to 400 KHz. In the topical application of localized magnetic fields by coils placed close to the skin, compliance with the MPRII guidelines may require use of a distributed coil, in order to keep the spatial maximum of the field from exceeding the MPRII limit. It is yet a further object of the present invention to provide distributed coils that induce localized magnetic fields.

The brain adapts to nuisance signals by plasticly changing neural circuitry, such as to block these signals from further processing. This effect has been noticed in electric field therapy of insomnia, where the effectiveness of a fixed frequency field wears off after several nights of application. It is an object of the present invention to provide a magnetic field with characteristics such as to minimize this adaptive effect.

SUMMARY

The vestibular nerves and several other types of somatic sensory nerves detect bodily motion, and code the information as frequency modulation (FM) of stochastic firing rates. These sensory signals can excite a resonance in the central nervous system, as is seen from the soothing effect of rocking a baby with a frequency near ½ Hz. The present invention provides a method and means for exciting this sensory resonance by application of an oscillatory external magnetic field with a dominant frequency near ½ Hz. It appears that such magnetic fields cause a weak frequency modulation of the firing rates of certain sensory receptors, most likely the vestibular end organ and muscle spindles. The resulting weak FM signals in the afferents from these receptors affect the central nervous system in much the same manner as a subliminal rocking motion.

For a sustained noticible effect the magnetic field intensity must be chosen such as to cause weak FM signals that have signal-to-noise ratios such that the signals go unchecked by nuisance-blocking circuitry, while still being strong enough to influence the autonomic nervous system through a resonance in certain critical neural circuitry. From experiments, this requirement on the signal-to-noise ratio appears to be met by magnetic field amplitudes in the range from 5 femtotesla to 50 nanotesla. Several different results can be obtained, such as relaxation, sleep, and sexual excitement, and control of tremors, seizures, and panic attacks, depending on the field application site and the frequency used.

The magnetic field may be produced by a coil connected to a voltage generator. It is important to curtail higher harmonics of the magnetic field wave form such as not to irritate the brain or pose a threat of kindling. To this end, the output wave form of the voltage generator must be subjected to a restriction, here phrased in terms of the spectral power density function.

For topical magnetic field application one needs coils which induce magnetic fields that fall off rapidly with distance. A design procedure for such multipole coils is discussed. A method is also provided for the design of multipole coils for which the windings are distributed in order to assure compliance with MPRII, when the coil is deployed close to the skin.

A magnetic field of desirable characteristics for inducing relaxation or sleep can also be generated by a mechanical apparatus that is driven by naturally occuring air motions or drafts. An embodiment comprises a permanent magnet that is mounted in the hollow of a sperically domed shell to which is fastened a silk flower on a stem of appropriate length, such as to give a natural rocking frequency near ½ Hz. Small air drafts cause the assembly to rock slightly, thereby tilting the magnet in an oscillatory motion. As a result, the magnetic field induced by the magnet has a flucuating component, which excites in nearby subjects the ½ Hz sensory resonance, if the device is properly tuned. The tuning is done by slightly doming, by an adjustable amount, the surface that supports the domed shell of the rocking assembly.

The invention lends itself to an embodiment as a nonlethal weapon which remotely induces wooziness in foes. The embodiment comprises a permanent magnet that is rotated by electric motor action by means of coils energized by a battery-powered pulse circuit tuned to a frequency appropriate to the ½ Hz sensory resonance. The activity and frequency schedule can be controlled by a programmable processor.

In social settings it is desirable to have the voltage generator and the coil contained in a single case, such as an eye shadow box. A compact magnetic field generator of this type can be carried in a purse or trousers pocket.

DETAILED DESCRIPTION

It has been found in our laboratory that a weak oscillatory external magnetic field can be used to excite the ½ Hz sensory resonance. Sinusoidal magnetic fields with an amplitude between about 5 femtotesla and 50 nanotesla have been observed to induce ptosis of the eyelids, relaxation, sleepiness, a "knot" in the stomach, a soft warm feeling in the stomach, a tonic smile, sudden loose stool, and sexual excitement, depending on the precise frequency used, the part of the body exposed, and the strength and duration of the field application. The frequencies that gave these effects are all close to ½ Hz. The effects are experienced after the subject has been exposed to the field for an extended time, ranging from minutes to hours. Even for optimum field frequency, the effects have been observed only for weak fields with amplitudes roughly in the range from 5 femtotesla to 50 nanotesla.

Human sensitivity to such weak magnetic fields with frequencies near ½ Hz is not understood, and appears to be in conflict with present neuroscience. However, the effects have been observed repeatedly and consistently over a period of a year and a half, in experiments in which the inventor served as the subject. The experiments may be briefly summarized as follows.

In the experiments, ptosis of the eyelids was used as a practical indicator for autonomic response. When voluntary control of the eyelids is relinquished, the eyelid position is determined by the autonomic nervous system [4]. There are two ways in which the indicator can be used. In the first, the subject simply relaxes control over the eyelids, and makes no effort to correct for any drooping. The more sensitive second method, here called "the eyes-up method", requires the subject to first close the eyes about half way. While holding this position, the eyes are rolled upward, while giving up voluntary control of the eyelids. With the eyeballs turned up, ptosis will decrease the amount of light admitted to the eyes, and with full ptosis the light is completely cut off. The second method is very sensitive because the pressure exerted on the eyeballs by partly closed eyelids increases parasympathetic activity. As a result, the eyelid equilibrium position becomes somewhat labile, a state that is easily recognized by eyelid flutter. The labile state is sensitive to very small shifts in the activities of the sympathetic and parasympathetic systems. The method works best when the subject is lying flat on the back and is facing a blank light color wall that is dimly to moderately lit.

The frequency at which ptosis is at a maximum is here called the ptosis frequency. It can be measured rather accurately with the eyes-up method, and it serves as a characteristic frequency for the ½ Hz sensory resonance. The frequencies at which the mentioned effects have been observed lie in the range from 20% below to 10% above the ptosis frequency. Although the ptosis frequency depends on the state of the nervous and endocrine systems, it always is near ½ Hz. It also has been found that the ptosis frequency is subject to a downward drift, rapid at first and slowing over time. The ptosis frequency can be followed in its downward drift by manual frequency tracking aimed at keeping ptosis at a maximum. Eventually the frequency settles to a steady value, after about 10 minutes of field application. The frequency for an early ptosis, typically 0.53 Hz, can be maintained in an approximately steady state by turning the field off as soon as the ptosis starts to decrease, after which the ptosis goes through an increase followed by a decline. The field is turned back on as soon as the decline is perceived, and the cycle is repeated.

The temporal behavior of the ptosis frequency is found to depend on the amplitude of the applied oscillatory magnetic field. At the low end of the effective intensity range, the ptosis frequency shift is less for smaller field amplitudes, and the shift becomes imperceptible at very weak fields of 5 femtotesla or so, where a faint ptosis can still be detected by a perceptive subject. The high end of the tentative effective intensity range has not been explored in this regard.

Use of square waves rather than sine waves for the time dependence of the magnetic field gives somewhat similar results, but there is a peculiar harsh feeling that is absent for sine wave stimulation. The harsh feeling is attributed to strong higher harmonics in the square wave.

The results have been obtained with systemic field applications as well as with topical applications of a localized magnetic field, either administered to the head or to body regions away from the head. Applications of sharply localized weak fields to body regions far away from the head show that the magnetic field acts on somatosensory nerves.

The effects induced by magnetic field application over an extended time interval often linger for as much as an hour after ending the application This suggests that the endocrine system is affected.

Experiments of magnetic field therapy for mild insomnia have been conducted for over 200 nights, using a variety of generators and coils. Among the various wave forms the sine wave has given the best results when used with very low field amplitudes, of the order of 10 femtotesla, applied to the lower lumbar region of the body. A typical frequency used in these experiments is 0.49 Hz. A virtue of the very small field amplitudes is that adaption to the stimulus is at a minimum, so that the treatment remains effective over many nights. Adaption is further mimimized by using multipole magnetic fields. Such fields are sharply localized, and they have strongly nonuniform spatial distributions. As a result, the evoked signals received by the brain from the various parts of the body are strongly nonuniform and localized. As a consequence, changes in sleep position cause a large variety of sensory patterns, with a limited duration for each individual pattern. An other successful approach for keeping down adaption is to limit the magnetic field application to half an hour or so; larger field strengths can then be used.

Experiments for inducing sexual excitement by application of sinusoidal magnetic fields have been performed using both topical and systemic field application. Topical application of a sinusoidal multipole magnetic field of order 6 to the lower lumbar region, with maximum field amplitude of about 1 nanotesla, usually causes an erection after about 13 minutes exposure, and the erection can be maintained as long as an hour. Effective frequencies depend on physiolgical conditions, but a typical effective frequency is 0.62 Hz.

Systemic application of an approximately uniform sinusoidal magnetic field at a frequency of 0.55 Hz and an amplitude of 2.3 nanotesla results in wooziness after about 2 hours exposure; sexual excitement sets in about 1 hour later. The sinusoidal magnetic field for this experiment was obtained simply by using a 33 rpm phonograph turntable which carries two permanent magnets with a total magnet moment of 6.5 $Am^2$; the distance to the subject was 10.4 m. Although the use of the 33 rpm turntable is convenient, the frequency of 0.55 Hz is not optimum for excitation of the ½ Hz sensory resonance. This explains the long exposure times needed to obtain a physiological response. Other experiments with systemic application of magnetic fields, albeit with slightly greater nonuniformity, have given results that are similar to those obtained with topical applications of sharply localized fields.

The finding that excitation of the ½ Hz sensory resonance results in different effects depending on the precise frequency near ½ Hz used shows that the resonance has fine structure. However, all the effects observed, i.e., ptosis of the eyelids, relaxation, sleepiness, a "knot" in the stomach, a soft warm feeling in the stomach, a tonic smile, sudden loose stool, and sexual excitement, involve the autonomic nervous system in one way or the other. Moreover, the frequencies for which the different effects are observed all lie close together near ½ Hz. It thus appears that the separate resonances in the fine structure involve the same neural and endocrine mechanism. The resonance phenomena, including their physiological consequences, will therefore be collectively referred to as "the ½ Hz sensory resonance".

The novel experiments and discoveries discussed above form the basis of the present invention, in which a time-varying magnetic field, with certain restrictions on the spectral power density and field strength, is applied for the purpose of influencing a subject's nervous system, by way of the ½ Hz sensory resonance. The spectral restriction entails limiting the spectral power density at frequencies in excess of 2 Hz to at least 20 dB below the spectral maximum, and requiring the spectral function maximum to lie in the frequency range 0.1 to 1 Hz. The spectral restriction is imposed for the purpose of avoiding both the risk of kindling and a harsh feeling, while it allows excitation of the ½ Hz sensory resonance, either by tuning or by choosing an appropriate temporal structure of the time variation of the field, such as a slightly chaotic frequency schedule. The peak-to-peak field strength of the time-varying magnetic field is restricted to the range 10 femtotesla to 100 nanotesla. For field strengths in this range, the evoked signal input to the brain has a signal-to-noise ratio which is small enough to not get checked by nuisance-guarding neural circuitry, while it is still large enough to cause long-term excitation of the resonant circuitry involved in the ½ Hz sensory resonance.

The characteristic time for the temporal behavior of the ptosis frequency, such as the initial frequency drift discussed above, is of the order of several minutes. This suggests that the ½ Hz resonance is modulated by a process, the rate of which is controlled by bulk substance release or uptake and perhaps a subsequent diffusion; candidates for the substance are neurotransmitters, second messengers, and hormones. The process whereby the ptosis frequency is influenced by the bulk substance release or uptake is here called chemical modulation of the resonance. It is expected that the substance concentration perturbations have other, "extended", physiological effects as well. For instance, pathological oscillatory activity of neural circuits, such as occurring in tremors and seizures, is influenced by the chemical milieu of the neural circuits involved. So are emotional disorders such as depression, mania, anxiety, and phobia. Hence, the manipulation of the autonomic nervous system by means of imposed oscillatory magnetic fields arranged to exite the ½ Hz sensory resonance may afford, through extended chemical modulation, some measure of control of these disorders, and of tremors and seizures as well. It is postulated here that such control is possible. The control, if administered properly, may provide a treatment of the disorders, through conditioning and other plastic modifications of neural circuit parameters.

The invention may be used to prevent elileptic seizures by switching on the magnetic stimulation when a seizure precursor or aura is felt by the patient. A somewhat similar use is seen for the prevention of panic attacks. [The excitation of the ½ Hz sensory resonance by a time-varying magnetic field can also be used as a modality for control and treatment of emotional disorders, through its influence on the endocrine system].

Figure 1:
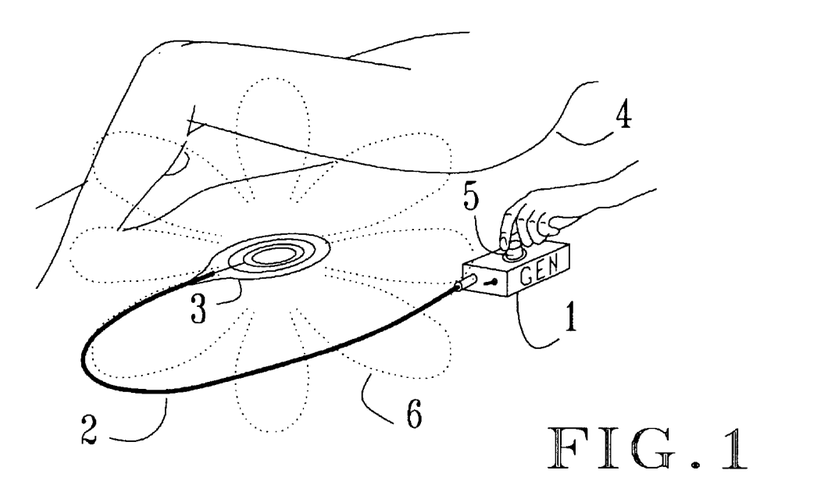
FIG. 1 illustrates the preferred embodiment for topical application of an oscillating magnetic field for ecxitation of the ½ Hz sensory resonance.

A preferred embodiment of the invention is shown in FIG. 1, where a voltage generator 1, labeled as "GEN", is connected through a thin coaxial cable 2 to a coil assembly 3; the latter is placed some distance beneath the subject 4 near the body region selected for topical application. The frequency of the voltage generator 1 can be manually adjusted with the tuning control 5, so that by manual scanning a frequency can be found at which the ½ Hz sensory resonance is excited. Upon being energized by the generator 1, the coil assembly 3 induces a magnetic field which at large distances is a multipole field with field lines 6. The voltage generator must be designed such that the output complies with the spectral restrictions discussed above; this can easily be done by those skilled in the art. The coil 3 can be conveniently placed under the mattress of a bed. As an alternative to manual tuning, the time-varying voltage output of the generator can be controlled automatically by a processor such as the Basic Stamp [5]; the processor is programmed to administer a suitable frequency schedule and on/off times. The setup of FIG. 1 has been employed in the insomnia therapy experiments and the sexual arousal experiments discussed.

Figure 2:
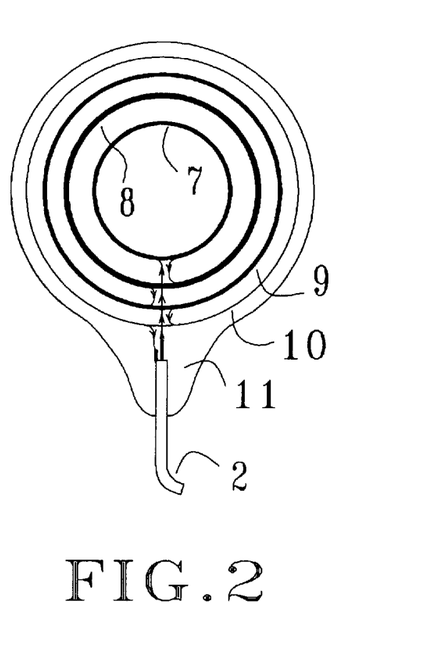
FIG. 2 shows a multipole coil for the generation of a localized magnetic field.

For topical magnetic field applications, such as illustrated by FIG. 1, it is important to have a sharply localized magnetic field, either to avoid unwanted exposure of body regions away from the region of application, or to decrease adaption, as discussed above. A planar coil assembly suitable for the induction of such a sharply-localized magnetic field is shown in FIG. 2. The assembly consists of four coils, referred to as 7, 8, 9, and 10, with alternating winding directions. The series assembly of coils is connected to the coaxial feed cable 2. The coils 7–10 are mounted on an adhesive sheet 11 of insulating material, and the assembly is covered by adhesive tape. The coil diameters are proportional to 1, √2, √3, 2, and the number of windings are respectively proportional to 4, −6, 4, −1, where positive numbers indicate clockwise windings, and negative numbers indicate counterclockwise windings. For clarity, the connecting wires between coils are shown as running at some distance from each other, but these wires should actually be laid very close together, in order that their induced magnetic fields cancel each other as much as possible. With this understanding, the coil assembly of FIG. 2 can be shown to induce at large distances r a magnetic potential $$\Psi = (630 \, \mu N_4 I/b \, 7)(R_1/r)^8 P_7(\cos\theta), \quad (1)$$

where $\mu (=4\pi \times 10^{-7}$ H/m for free space) is the permeability, $N_4$ the number of windings of the fourth coil, I the current through the coil assembly, $R_1$ the radius of the first coil, $P_7$ the Legendre polynomial of degree 7, and $(r,\theta,\phi)$ the polar coordinate system centered at the coil center, with the direction $\theta = 0$ taken along the coil axis [6]. From (1) the magnetic field B can be calculated as $$B = -\mathrm{grad}\Psi. \quad (2)$$

From (1) and (2), one has for the coil of FIG. 2, with $R_1 = 2$ cm, and $N_4 = 2$, at a point on the coil axis a large distance z from the coil plane, for $z/R_1 \gg 1$, the approximation $$B = 4.63 \times 10^{-17} I/z^9 \text{ tesla}, \quad (3)$$

where the current I is in ampere, and the distance z is in meters. Eq. (3) shows that the far magnetic field falls off as the inverse ninth power of distance, so that the field is sharply localized. For a current of 0.3 mA, at a distance of 10 cm from the coil, Eq. (3) gives B=13.9 pT, which is sufficient for a physiological effect when properly tuned; at 30 cm distance the field is 0.7 fT, too small to have physiological influence.

Coils for induction of localized and nonuniform magnetic fields may be designed with the following general procedure. The field at a point P on the axis of a circular current loop of radius R is $$B_z = \mu I R^2 / 2\rho^3, \quad (4)$$

where $\mu$ is the permeability, I the loop current, $\rho^2 = R^2 + z^2$, and z is the distance from point P to the loop plane. Expanding the factor $1/\rho^3$ as a power series in $R^2/z^2$ results in a multipole expansion of the field (4). Consider in a plane an assembly of m concentric current loops with radii $R_j$ and currents $I_j$, j=1 to m. In the multipole expansion of the total magnetic field induced on the axis of the current loop assembly, the m−1 lowest multipole contributions can be made zero by choosing the loop radii and loop currents such as to satisfy the equations $$\Sigma R_j^2 I_j = 0, \Sigma R_j^4 I_j = 0, \ldots, \Sigma R_j^{2m-2} I_j = 0, \quad (5)$$

where the summations extend from j=1 to j=m. Equations (5) form a Van der Monde system [7]. Solutions provide radius ratios $R_j/R_1$, and current ratios $I_j/I_1$ for j=2 to m. In practice the current ratios are chosen as integers, so that the current loops can be implemented as coils with integer numbers of windings, with the coils placed in series with each other. A solution of this type is easily constructed for any m, from a modification of the Pascal triangle for the binomial coefficients. The modification entails starting each row of the triangle with the row number, and completing the row by the well-known Pascal triangle construction. One thus finds for the first row 1, for the second row 2,1, for the third row 3,3,1, for the fourth row 4,6,4,1, etc. For a assembly of m individual coils, the modified Pascal triangle must be completed up to row m. The number of windings, $N_j$, of the individual coils j, j=1 to m, are then to be taken proportional to the sequence of numbers in the mth row of the triangle, with alternating signs. The squared radii, $R_j^2$, of the individual coils are to be taken proportional to the index j. With $I_j=IN_j$, where I is the current through the coil assembly, the $R_j$ and $I_j$ satisfy (5), as can be verified by substitution, for any chosen value of m.

With equations (5) satisfied, the total magnetic field induced by the m coils falls off as inverse distance raised to the power 1+2m, far away on the axis of the coil assembly. Continuation of the field off the axis then gives as dominant asymptotic field a multipole magnetic field of order 2m. The procedure was followed in the design of the coil of FIG. 2, with m=4. Coil assemblies that induce at large distance a multipole magnetic field with a pole of order larger than 2 are here called multipole coils. It is emphasized that the multipole coil design must be implemented acurately in order that the lower-order multipole contributions cancel sufficiently to provide at large distance the desired multipole field. The individual coils of the multipole coils discussed above have circular shape, but other shapes such as squares may be chosen as well. The far field would then not be axisymmetric, and would thus involve spherical harmonics [6].

Figure 3:
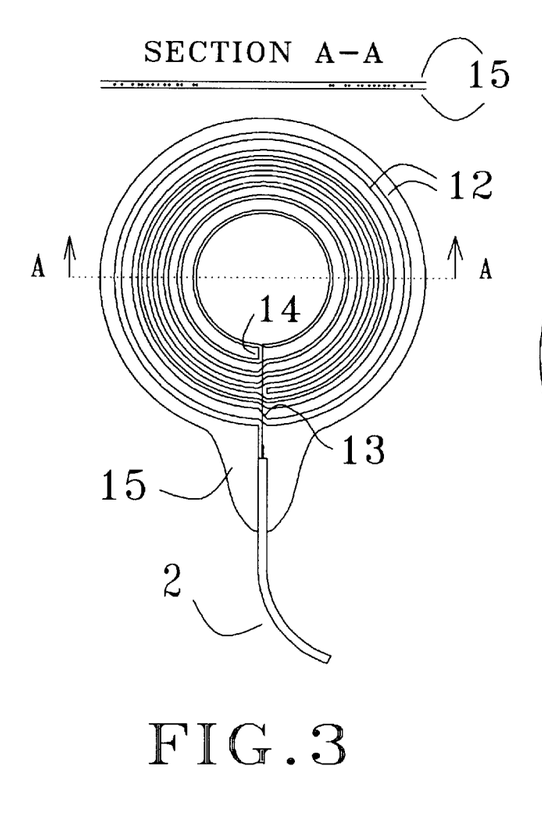
FIG. 3 shows a distributed coil for close proximity topical magnetic field application.

For compliance with the MPRII guidelines for limitations of the exposure to low frequency electromagnetic fields, a planar multipole coil which is to be used directly on the skin may need to have distributed windings. FIG. 3 shows such a coil, which includes circular wire windings such as 12, with connecting wires such as 13 and 14, that provide either a continuation of the same winding sense to the next circular winding, such as connection 13, or else provide an oposite winding sense, such as connection 14. The connecting wires have been drawn such as to show clearly the connections to the current loops; in practice, all connecting wires should be laid closely alongside the radial wire from the center conductor of the coaxial cable 2 to the smallest winding, in order that the magnetic fields induced by the currents in these wires cancel each other as closely as possible. The magnet wire windings are sandwiched between two sheets of insulation 15. The serially connected windings are fed by the thin coaxial cable 2. The radii $R_j$ of the windings have been chosen such that the coil induces a magnetic field that asymptotically falls off as the distance to the inverse 7th power, i.e., as the field of a multipole of order 6. This is here achieved by having the radii of the circular windings respectively proportional to the numbers in the sequence 0.8165, 0.8564, 1.0000, 1.0488, 1.1547, 1.2111, 1.2910, 1.3540, 1.4142, 1.4832, 1.5275, 1.6021, 1.7321, and 1.8166.

The distributed multipole coil of FIG. 3 was designed by distributing, in a multipole coil with m=3, each of the coils with multiple windings to several single windings, without violating Eq. (5). A planar circular multiplet coil with m=3 has three concentric individual coils j, j=1 to 3, with normalized squared radii, $R_j^2/R_1^2$ equal to j, and normalized winding numbers, $N_j/N_3$, respectively equal to 3,-3,1. For m=3, Eqs. (5) read $$\Sigma R_j^2 I_j = 0, \Sigma R_j^4 I_j = 0, \quad (6)$$

where the sums extend over j=1, 2, 3. A solution of Eqs. (6) is provided by planar concentrated windings with squared radii, $R_j^2$ proportional to the sequence 1,2,3, and winding numbers $N_j$ proportional to 3,-3,1, as given by the 3d row of the modified Pascal triangle. The first coil, with j=1, is now spilt into 3 separate single circular windings of squared radii 1-Δ, 1, and 1+Δ. Likewise, the second concentrated coil, with j=2, is split into 3 separate single circular windings with squared radii 2-Δ, 2, and 2+Δ. The third concentrated coil, j=3, is left unchanged. One thus arrives at the coil assembly with squared radii proportional to the sequence 1-Δ, 1, 1+Δ, 2-Δ, 2, 2+Δ, 3, and with currents proportional to 1, 1, 1, -1, -1, -1, 1. Substitution into Eqs. (6), with the sums extending over j=1 to 7, shows these equations to be satisfied for any value of Δ. An equidistant sequence of squared radii is obtained for Δ=⅓, with the result that the $R_j^2$ are proportional to the sequence $$0.6667, 1.0000, 1.3333, 1.6667, 2.000, 2.3333, \text{ and } 3.0000. \quad (7)$$

Coil assemblies may be composed by taking linear combinations of $R_j^2$ sequences; Eqs. (6) then remain valid for the composite coil assembly. A linear combination of two identical sequences (7), with coefficients 1 and 1.1, gives $R_j^2$, j=1 to 14, proportional to the sequence 0.6667, 0.7333, 1.0000, 1.1000, 1.3333, 1.4667, 1.6667, 1.8337, 2.0000, 2.2000, 2.3333, 2.5663, 3.0000, and 3.3000. The corresponding currents are 1, 1, 1, 1, 1, 1, -1, -1, -1, -1, -1, -1, 1, and 1. Taking square roots of the $R_j^2$ sequence gives the circular current loop radii $R_j$ shown above and implemented in the distributed multipole coil of FIG. 3.

The procedure may be generalized to design a distributed planar circular multipole of any even order 2m. Each of the individual coils with multiple windings is spread into $N_j$ separate single windings with squared radii $R_{jk}^2$, k=1 to $N_j$, proportional to an equispaced sequence centered on $R_j^2$, and with spacing $\Delta_j$. The spacings $\Delta_j$, j=1 to m-1, can be chosen such that Eqs. (5) are satisfied and bunching of the individual windings is minimized. If desired, linear combinations of the resulting coils can be constructed. For m smaller than 5, the equations for $s_k^2$ are linear; for m 5 or 6, they are quadratic and can still be solved easily. For m larger than 6, the equations can be solved by numerical methods. In practice, one rarely needs to go beyond m=4, since the multipole of order 8 gives adequate localization of the induced magnetic field.

Figure 4:
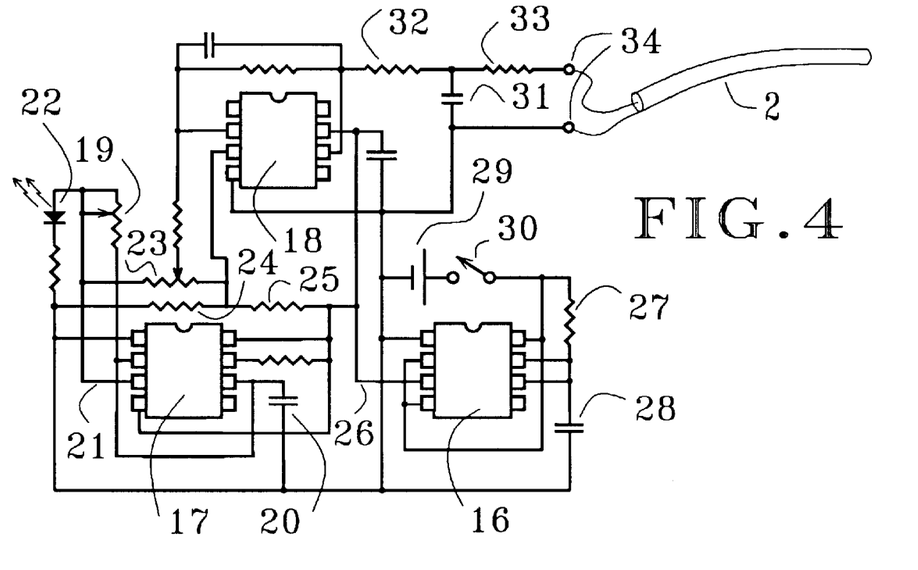
FIG. 4 shows a near-sine wave generator with automatic shutoff.

A simple near-sine wave generator which satisfies the spectral restrictions of the invention is shown in FIG. 4. The battery powered generator is built around two RC timers 16 and 17, and an operational amplifier 18. Timer 17 (Intersil ICM7555) is hooked up for astable operation; it produces a square wave voltage with a frequency determined by potentiometer 19 and capacitor 20. The square wave voltage at output 21 drives the LED 22, and serves as the inverting input for the amplifier 18 (MAX480), after voltage division by potentiometer 23. The noninverting input of amplifier 18 is connected to an intermediate voltage produced by resistors 24 and 25. Automatic shutoff of the voltage that powers the timer and the amplifier, at point 26, is provided by a second timer 16 (Intersil ICM7555), hooked up for monostable operation. The shutoff occurs after a time interval determined by resistor 27 and capacitor 28. Timer 16 is powered by a 3 volt battery 29, controlled by a switch 30. The amplifier 18 is hooked up as an integrator. Additional integration is performed by the capacitor 31 and resistor 32. The resistor 33 limits the output current to the terminals 34 that are connected to the coil assembly by the coaxial cable 2.

Figure 5:
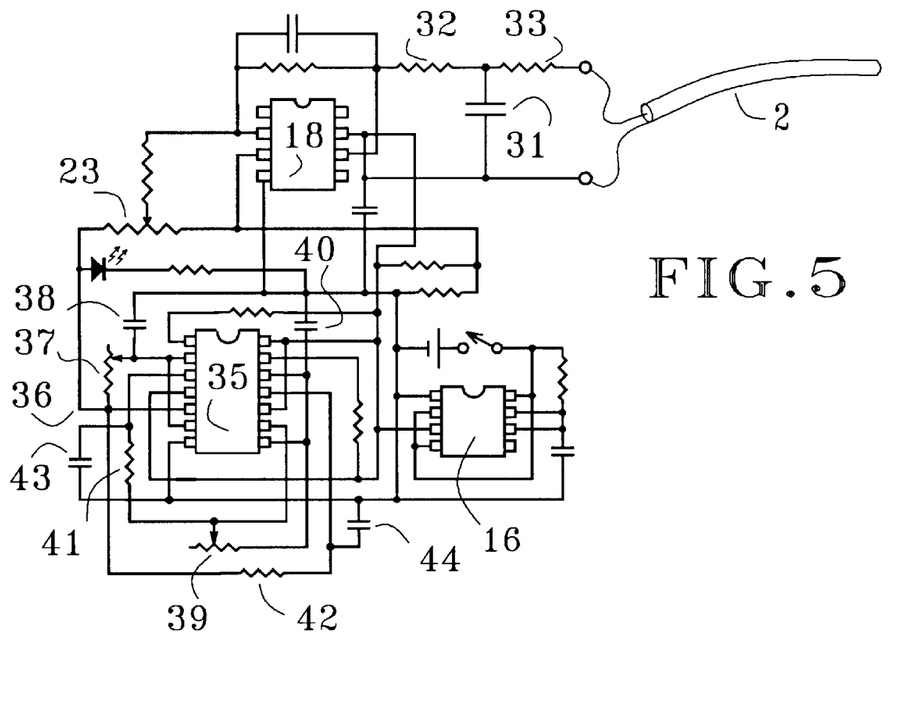
FIG. 5 shows an embodiment that generates a chaotic magnetic field.
Figure 6:
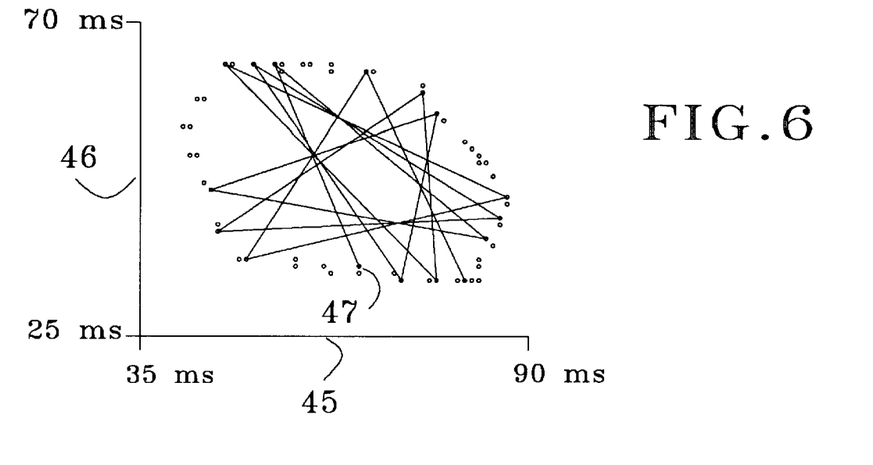
FIG. 6 shows transitions of a chaotic square wave.

Two problems are encountered when a sinusoidal magnetic field is used for excitation of the sensory resonance near ½ Hz. After the resonance is first established, the resonant frequency slowly drifts downward, so that the voltage generator has to be retuned frequently in order that the resonance be maintained. This manual tracking of the resonant frequency is an inconvenience to the subject. The other problem encountered is an adaption of the central nervous system to the signals evoked by the magnetic field. The time to adaption depends on the strength of the FM signals evoked by the oscillating magnetic field, as compared with the relevant noise. For large signal-to-noise ratio (S/N), the evoked signal is quickly recognized by the brain as an irrelevant nuisance, and the evoked signals are blocked from further processing. For very small S/N no effect is felt. There is an intermediate range of S/N for which the evoked signals, although not recognized as a nuisance, are strong enough to excite the sensory resonance. By continuity, one expects that there is an optimum S/N for effective magnetic field application for purposes of exciting the ½ Hz sensory resonance. It has been found however, that repeated application at the optimum S/N still illicits a slow adaption. The adaption can be circumvented by using topical application to different body sites. There further is merit in using a magnetic field that is not precisely sinusoidal, but has a weakly stochastic nature, with a narrow power spectrum around the resonant frequency. A generator that produces such a weakly stochastic nearly harmonic voltage is shown in FIG. 5. The generator contains a dual timer 35 (Intersil ICM7556) that is hooked up such as to produce a chaotic square wave at point 36. Both sections of the dual timer 35 are hooked up for astable operation, with slightly different RC times. The RC time of the first timer section is determined by the resistor 37 and capacitor 38. The RC time of the second timer section determined by the resistor 39 and the capacitor 40. The two timer sections are coupled by connecting their outputs crosswise to the threshold pins, via resistors 41 and 42, with capacitors 43 and 44 to ground. For a proper range of component values, easily found by trial and error, the square wave output of each of the timer sections is chaotic. The component values can be adjusted experimentally to provide a chaotic output with acceptable characteristics. An example for the chaotic output is shown in FIG. 6, where the points plotted correspond to transitions (edges) of the square wave. Abscissa 45 and ordinates 46 of a plotted point are time intervals between consecutive transitions of the square wave output; for any transition, the abscissa is the time to the preceding transition, and the ordinate is the time to the nect transition. Starting with transition 47, consecutive transitions are found by following the straight lines shown. The transition times follow a pseudo random sequence, with some order provided by the oval attractor. The results shown in FIG. 6 were derived from the voltage measured at point 36 of the device of FIG. 5, with the following component values: $R_{37}$=1.22 MΩ, $R_{39}$=1.10 MΩ, $R_{41}$=440 KΩ, $R_{42}$=700 KΩ, $C_{38}$=0.68 μF, $C_{40}$=1.0 μF, $C_{43}$=4.7 μF, and $C_{44}$=4.7 μF. In the above list, $R_i$ is the resistance of component i in FIG. 5, and $C_j$ is the capacitance of component j. The chaotic square wave at point 36 is used, after voltage division by potentiometer 23, as input for the micropower operational amplifier 18 (MAX480) hooked up as an integrator. Additional integration is performed by the capacitor 31 and resistor 32. The output current to the coil via the coaxial cable 2 is limited by resistor 33.

Figure 7:
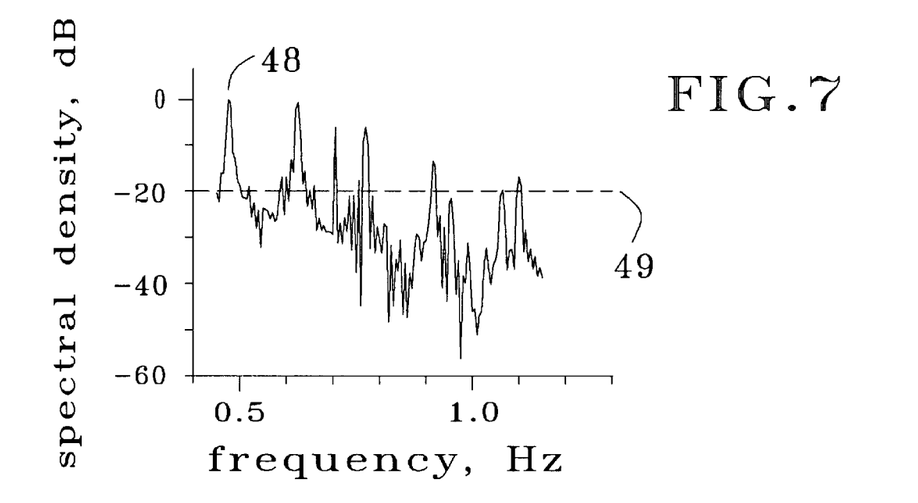
FIG. 7 shows the power spectrum of the magnetic field produced with the generator of FIG. 5.

FIG. 7 shows part of the spectral power density function (also called "spectral density") of the voltage produced by the generator of FIG. 5, with the component values mentioned. The spectral power density is shown in dB below the maximum 48 which occurs at a frequency of 0.42 Hz. In order to prevent kindling [4] and irritating the brain, the spectral density should, for all frequencies in excess of 2 Hz, be more than 20 dB below the spectral maximum. In FIG. 7, the −20 dB line is shown as 49.

Figure 8:
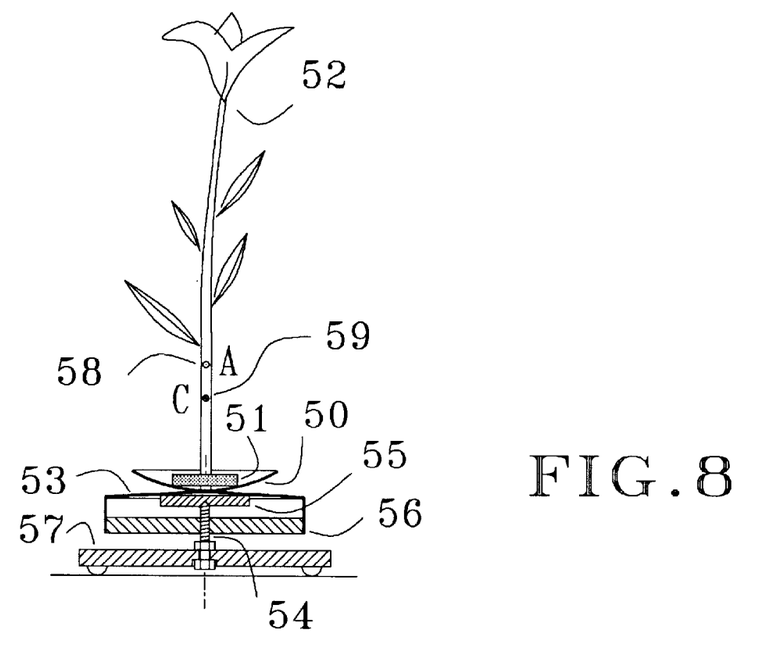
FIG. 8 shows an aero-mechanical embodiment for generating a fluctuating magnetic field for inducing relaxation and sleep.

The magnetic field for exciting the ½ Hz sensory resonance need not be generated by currents in a coil; instead it may be provided by a permanent magnet that is moved such as to cause dipole radiation. FIG. 8 shows such an embodiment in the form of a aero-mechanical device for generating a fluctuating magnetic field for inducing relaxation and sleep. The idea is to rock a permanent magnet by means of a mechanical oscillator that is aerodynamically excited by small air currents that are present at the device. The magnet then induces a fluctuating magnetic field by virtue of its rocking motion. The device of FIG. 8 includes a mechanical oscillator in the form of a rocker comprised of a hard domed shell 50 to which is fastened a permanent magnet 51 and a silk flower 52. The rocker rests upon a nonferromagnetic thin hard shell 53, which for tuning purposes is domed to an adjustable extent by a screw 54 and a pressure plate 55. Small oscillations of the rocker are excited by aerodynamic forces that act on the silk flower 52 by virtue of small air currents and drafts at the location of the device. The screw 54 engages a nonferromagnetic plate 56, which is fastened to the shell 53. The screw 54 is maintained in the base plate 57. By turning the assembly of plate 56 and shell 53 with respect to the base plate 57, the natural oscillation frequency of the rocker can be tuned. The design of the device may be done as follows. Let $R_d$ and $R_s$ be respectively the radii of curvature of the outer surface of dome 50 and shell 53. Let point A, denoted as 58, be the center of curvature of the dome surface, and let point C, denoted by 59, be the center of mass of the rocker. The natural frequency of the rocker, for small excursions, is readily found to be $$f = \frac{1}{2\pi}\sqrt{\left\{(g/R_d)\frac{\gamma - \alpha(1-\gamma)}{\xi - (1-\gamma)^2(1+\alpha)}\right\}}, \tag{8}$$

where g is the acceleration of gravity, γ the distance between points A and C divided by $R_d$, α the ratio of $R_d$ to $R_s$, and ξ is the square of the radius of inertia of the rocker with respect to the center of mass 59, divided by the square of $R_d$. In (8), the terms proportional to (1−γ) are due to the translations of the center of mass that accompany the rocker rotations. Eq. (8) shows how to design the device such that the natural frequency f is near ½ Hz. The frequency can be tuned by adjusting the radius of curvature $R_s$ of the shell, by the screw arrangement shown in FIG. 8; this changes the ratio α in (8). The aerodynamic forces acting on the silk flower by air drafts have a wide frequency spectrum determined by air velocity fluctuations and the shedding frequency of vortices off the silk flower. For a device with small damping, the rocker response favors frequencies near the natural frequency, so that the power spectrum of the rocker oscillation is dominated by frequencies near f of (8). The resulting small stochastic oscillation of the permanent magnet causes a fluctuating magnetic field that decreases as the inverse third power of distance to the device. Measurements near a properly tuned device subject to typical residential air currents show an rms magnetic field strength of $13/r^3$ pT at a distance r from the device. An rms magnetic field fluctuation of 1 pT, which is plenty for occurrence of physiological effects, will be induced at a distance of 2.3 m.

Figure 9:
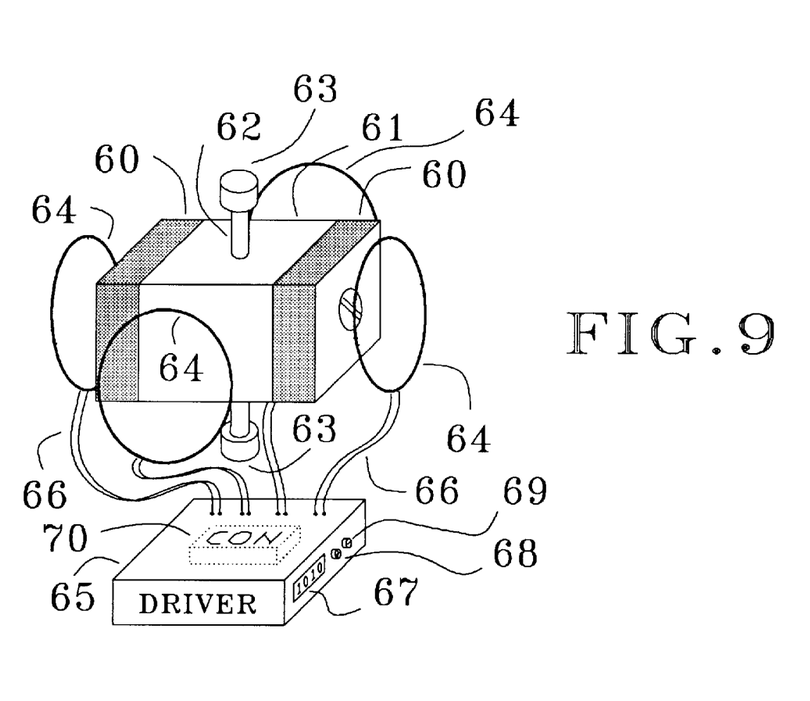
FIG. 9 shows an embodiment as a nonlethal weapon for projecting an oscillating magnetic field to cause drowziness in a foe.

Another embodiment in which a moving magnet is used to induce the time-varying magnetic field that is to excite the ½ Hz sensory resonance is a rotating magnet assembly. The magnet rotation is brought about by coils that receive voltage pulses of appropriate phase. Because very large magnetic moments are easily obtained with permanent magnets, this embodiment lends itself for projection of near ½ Hz oscillating magnetic fields over several hundred meters. In view of the possibility to remotely induce drowsiness in subjects at such distances, the embodiment can be used as a nonlethal weapon. A suitable arrangement is shown schematically in FIG. 9. Two permanent magnets 60 are mounted on an iron spacer 61, which is fastened to a shaft 62 that can rotate freely in bearings 63. Coils 64 are mounted such as to cause the magnet assembly to engage in a continuous rotation, when pulsed electric currents are passed through the coils in properly phased manner. The currents are caused by a driver 65 connected to the coils by wires 66. The period of rotation of the magnet assembly is determined by the pulse frequency of the driver, shown by the display 67; the period can be changed by operating up and down buttons 68 and 69. The driver may include a control unit 70 to provide a chosen schedule of activity times and frequencies. The driver and the control unit can be readily designed around a processor such as the Basic Stamp [5], by those skilled in the art. A compact and rugged device of this kind can be delivered to enemy teritory by mortar or air drop. The rotating magnet assembly will induce at a point P at a distance of r meters from the device a periodic magnetic field with peak to peak strength $$B = 4\mu M/(4\pi r^3) \text{ tesla,} \quad (9)$$

where M is the magnetic moment of the magnet assembly in $Am^2$. Eq.(9) is valid for remote points P in or near the plane through the center of the magnet assembly, perpendicular to the axis of rotation of the magnet assembly. For a device 5 cm in overall diameter, the magnetic moment M can easily be made as large as 13 $Am^2$. A periodic magnetic field with peak-to-peak strength of 0.19 pT, sufficient for causing drowsiness, is then induced at a distance r=300 m from the device.

Figure 10:
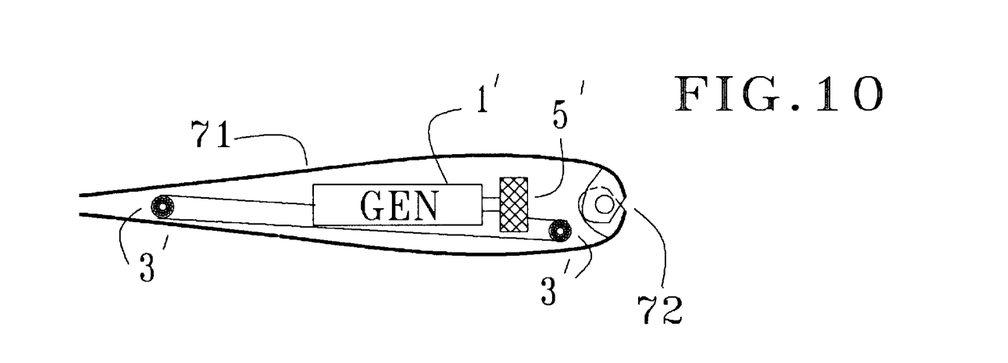
FIG. 10 shows a compact embodiment in a hinged eye shadow box.

In some social settings it is important that the magnetic field stimulus can be applied inconspicuously. A compact device for this purpose is shown in FIG. 10, where an eye shadow case 71 with hinge 72 contains both the voltage generator 1' and the coil 3'. The tuning control 5', the power switch, monitoring LED, and 3 V Lithium coin-type battery are accessible after opening the clam-type case. The case can be carried in a purse or trousers pocket, and can be used for months on a single battery.

As noted above, human sensitivity to the very weak magnetic fields with a frequency near ½ Hz is not understood at present. However, several pieces of the puzzle can be clarified, as follows.

1) Localized topical application of the oscillatory magnetic field is afforded by multipole coils which induce fields that fall off sharply with distance. For instance, the coil assembly of FIG. 2 provides a magnetic pole of order 8, so that the asymptotic field falls off as the inverse 9th power of distance. This affords application of the magnetic field to small regions of the body away from the head, while the magnetic field exposure of the brain is entirely negligible. Hence, in these experiments the physiological effect is not due to magnetic fields acting directly on the brain; also, because of the field localization, the effects are not due to transmission to the brain of directly-induced (i.e., nonphysiological) electric currents by high-conductivity paths provided by blood vessels, lymph vessels, and spinal fluid. Thus the physiological effects in these cases are obtained strictly via somatosensory pathways, and it follows that the weak oscillatory magnetic field with frequency near ½ Hz directly affects certain somatosensory receptors. What kind of receptors are these, and what is the mechanism of susceptibility? A direct static response to the magnetic field itself is ruled out, since, unlike honeybees [8], man has no innate abilty to navigate by the earth's magnetic field. What remains is the notion of sensory receptors responding to the electric fields and eddy currents induced by the magnetic field oscillations. Order-of-magnitude calculations show that these electric fields and eddy currents are far too small to serve as a trigger for neuronal firing; the only way in which receptors can be influenced by the minute induced electric fields and currents is in a gradual manner, as in frequency modulation of spontaneous stochastic firing. But that is precisely the information coding employed by the receptor types involved in the ½ Hz sensory resonance, discussed in the Background Section: vestibular end organs, muscle spindles, Ruffini endings, and cutaneous cold and warmth receptors; all these receptors use frequency coding of the sensed information. Which of these receptors is most likely to be sensitive to the electric fields and eddy currents induced by the magnetic field oscillations? We will return to this question after considering several other aspects of the problem.

2) Since the eddy currents induced by the oscillatory magnetic field are proportional to the time derivative of the field, it is of interest to investigate the physiological effect of the rise time of square wave magnetic fields. Experiments show that the rise time does not affect the magnitude of the physiological response, but only its quality; short rise times give a harsh feeling that is absent for large rise times or sinusoidal field variation. It thus appears that the eddy currents, or the concomitant electric fields in the body, mainly affect the experienced response through their integrals over time.

Two candidates for a mechanism with such behavior come to mind, long-term charge accumulation at high-resistivity structures by eddy currents, and excitation of resonant neural circuits by afferent signals. The first mechanism would require charge relaxation times of the order of or larger than the period of the oscillatory magnetic field, say, 2 seconds; this condition is not satisfied in the tissues involved. The other mechanism considered is the excitation of a harmonic oscillator by a forcing function with a frequency near resonance. For small damping (high Q), the oscillator may get excited, over several cycles, to appreciable amplitudes, by coherently absorbing energy from "the forcing function". For high Q, considerable amplitudes result even in the presence of noise, if the forcing function contains a substantial Fourier component near the resonant frequency. The system acts as a sharp bandpass filter followed by an amplifier, much as the regenerative circuit of early radio. In case of a square wave forcing function, the response of the system is not influenced much by the rise time of a square wave, but is essentially determined by the forcing function integral over a quarter cycle. This is the sought-after response.

3) A physiological response occurs only for weak magnetic fields. More precisely, the frequency modulation of neuronal firing evoked by the imposed oscillatory magnetic field and presented to the brain by afferents must lie in a range that is limited below by modulations that are so weak as to be indiscernible from the noise, even by the exquisitely sensitive neural resonant circuitry involved, while the range is limited from above by modulations that are strong enough to be recognized by the brain as an irrelevant nuisance, and are therefore blocked from higher processing. The lower limit exists in every analog signal processor. That an upper limit exists as well is shown by experiments which employ moderately strong magnetic fields at the resonant frequency; no physiological response is observed in these cases. Thus emerging is a model in which the weak oscillatory magnetic field causes a frequency modulation in the firing of somatosensory receptors, so weak as to be burried in the noise; the faint FM signal causes resonance in a high-Q neural circuit, if the field frequency is near the resonant frequency of the circuit. The signal-to-noise ratio of the frequency modulation is so small as to not arouse a nuisance-blocking action by guard circuits.

4) The direct, i.e., non-physiological, effect of the imposed oscillatory magnetic field can be described as follows. Eddy currents are induced in the body by the electric field that results from oscillating magnetic fluxes and also from polarization charges that accumulate on the body surface and high-resistivity membranes. Charge concentrations in tissue relax with a time constant $$t_c = \epsilon/\sigma, \qquad (10)$$

where $\epsilon$ is the permittivity and $\sigma$ is the conductivity of the tissue. In biological tissue, the charge relaxation time $t_c$ is very much shorter than the oscillation period of our magnetic field. Hence, polarization charges that accumulate at the boundaries of high-resistivity regions, such as membranes and skin surfaces, may be considered to be in quasi-steady state, i.e., they are essentially in equilibrium. It follows that these surface charge distributions are such that the total electric field component normal to the surface vanishes; the eddy current at the surface then flows tangentially, as required by the steady state of the surface charge density. Thermal motion smears the surface charge into a thin layer with thickness of the order of the Debye length [9]. In the Debye layer, the perturbed ion concentrations provide a local pH perturbation. Such local pH perturbations have an effect on the folding of certain proteins through the interplay of hydrophobic molecular groups and pentagonal water [10]. Such folding is expected to play an important role in mechanoreceptors such as vestibular hair cells and muscle spindles. One may expect that the sensitive pH dependence of the folding makes these mechanoreceptors susceptible to weak imposed electric fields. Such susceptibility, with great sensitivity, has indeed been observed by Terzuolo and Bullock [11] for the nonadapting stretch receptor of Crustacea, nearly 4 decades ago. A similar sensitivity to electric fields and currents may be expected for vestibular hair cells. Such sensitivity is postulated here.

5) Another consideration points to the same receptors. Some aquatic animals have an exquisite sensitivity to external electric fields [12,13]. For example, it has been shown that dogfish, when in a drowsy state, can respond by eyelid movements (ptosis!) to a uniform electric field of 10 microvolt per meter, switched on and off with a frequency of 5 Hz [14,15]. An even greater sensitivity, down to 1 microvolt per meter, has been observed by monitoring heart rates [16,17]. It is noted in passing that both the ptosis and the heart rate response involve the autonomic nervous system of the fish. The pertinent sensory systems involve magnification of the external electric field by high-conductivity paths in a high-restitivity surround (by the Ampullae of Lorenzini [14]), specialized receptors, and dedicated neural circuitry. The receptor sensitivity appears to be comparable to that of our finest, the vestibular hair cells.

6) Looking, in man, for structures that provide a function similar to the electric field magnification discussed under 5), two structures stand out: muscle spindles and the semicircular canals of the vestibular organ. Afferent endings of muscle spindles form spirals around intrafusal fibers [4], and therefore provide a coil along which the emf due to oscillating magnetic flux is integrated. The semicircular vestibular canals are filled with endolymph [4], which has high electric conductivity; hence, comparatively large eddy currents are induced by the magnetic flux changes through the area encircled by the semicircular canal. As a result, nearly all of the emf induced along the canal is presented across the cupula that holds the vestibular hair cells. It follows that the resulting local pH perturbations at the receptors are magnified as a result of the special structures involved.

In view of the considerations 1) to 6), it appears that likely candidates for receptors which respond to the small electric fields and eddy currents induced by the magnetic field oscillations involved in the experiments discussed are the vestibular end organ and muscle spindles. It is here postulated that these receptors do indeed respond to the oscillatory magnetic field by slight frequency modulation of their spontaneous firing.

The invention is not limited by the embodiments shown in the drawings and described in the description, which are given by way of example and not of limitation, but only in accordance with the scope of the appended claims.

REFERENCES

[1] H. G. Loos, "Method and Apparatus for Modulating Cutaneous Nerves", U.S. patent application Ser. 08/447, 394, 1995.

[2] P. Lindemann, The Megabrain Report, Vol. 1, #2, p. 34–35, (1990), P.O. Box 6567, Los Angeles, Calif. 90065.

[3] P. Lindemann, The Megabrain Report, Vol. 1, #1, p. 30–31, (1990)

[4] E. R. Kandel, J. H. Schwartz, and T. M. Jessel, PRINCIPLES OF NEURAL SCIENCE, 3th edition, Elsevier, N.Y., 1991

[5] Basic Stamp, PARALAX, INC. Rocklin, Calif. 95765.

[6] P. M. Morse and H Feshbach, METHODS OF THEORETICAL PHYSICS, McGraw-Hill, New York, 1953

[7] G. H. Golub and C. F. Van Loan, MATRIX CALCULATIONS, 2nd Ed., John Hopkins University Press, Baltimore, 1991

[8] C-Y Hsu and C-W Li, "Magnetoreception in Honeybees", Science 265, 95 (1994)

[9] S. Ohki and H. Oshima, "Donnan Potential and Surface Potential of a Charged Membrane and Effect of Ion Binding on the Potential Profile", in ELECTRICAL DOUBLE LAYERS IN BIOLOGY, Ed. M. Blank, Plenum Press, New York, 1986

[10] D. W. Urry, "Elastic Biomolecular Machines", Scientific American January 1995, p. 64

[11] C. A. Terzuolo and T. H. Bullock, "Measurement of Imposed Voltage Gradient Adequate to Modulate Neuronal Firing", Proceedings of the National Academy of Sciences U.S.A., Physiology, 42, 687 (1956)

[12] J. Bastian, "Electrosensory Organisms", Physics Today, p. 30, February 1994

[13] ELECTRORECEPTION, T. H. Bullock and W. Heiligenberg, eds., Wiley, N.Y., 1986

[14] R. W. Murray, in HANDBOOK OF SENSORY PHYSIOLOGY, Vol. III/3, Eds. D. Autrum et all, Springer, N.Y., 1974
[15] S. Dijkgraaf and A. J. Kalmijn, "Verhaltungsversuche zur Function der Lorentzinischen Ampullen", Naturwissenschaften 49, 400 (1962)
[16] A. J. Kalmijn, "Electroreception in sharks and rays", Nature (Lond.) 212, 1232 (1966)
[17] S. Dijkgraaf and A. J. Kalmijn, "Versuche zur Biologischen Bedeutung der Lorenzinische Ampullen bei den Elasmobranchiern", Z. vergl. Physiol. 53, 187 (1966).

I claim:

1. Apparatus for excerting an influence on the nervous system of a nearby subject, in the presence of atmospheric air currents, the apparatus comprising:
   mechanical oscillator;
   aerodynamic excitation means for providing excitation of the mechanical oscillator in response to said atmospheric air currents;
   permanent magnet means for providing a magnetic dipole, the magnetic dipole having an orientation;
   mounting means for mounting the permanent magnet means onto the mechanical oscillator in such a manner that said excitation causes a fluctuation of the orientation of the magnetic dipole;
   whereby a time-varying magnetic field is produced in the subject.

2. Apparatus according to claim 1, further including tuning means for tuning the mechanical oscillator.

3. A method for influencing the autonomic nervous system of a subject, comprising:
   applying to the subject a periodic magnetic field with a frequency in the range 0.1 to 1 Hz and an amplitude in the range 5 femtotesla to 50 nanotesla;
   determining, through manual frequency scanning, a frequency at which the subject experiences ptosis of the eyelids, the last said frequency being called the ptosis frequency; and
   setting the field frequency to a value in the range from 20% below to 10% above the ptosis frequency;
   whereby said periodic magnetic field will influence the autonomic nervous system of the subject.

4. Apparatus for exciting in a subject the ½ Hz sensory resonance having at a resonance frequency, the apparatus comprising:
   generator means for generating a time-varying voltage with a dominant frequency in the range 0.1 to 1 Hz;
   coil means, connected to the generator means, for inducing in the subject a magnetic field;
   tuning means for tuning the dominant frequency to said resonance frequency.

5. Apparatus according to claim 4, wherein the coil means comprise a multipole coil for inducing a localized magnetic field.

6. Apparatus according to claim 5, wherein said multipole coil includes distributed windings for limiting the exposure of the subject to the magnetic field.

7. Apparatus according to claim 4, also including:
   control means for automatically controlling the time-varying voltage.

8. A method for exciting in a subject the ½ Hz sensory resonance having at a resonance frequency, the method comprising the steps of:
   generating a time-varying voltage with a dominant frequency in the range 0.1 to 1 Hz;
   connecting the time-varying voltage to a coil; and
   tuning the dominant frequency to said resonance frequency.

* * * * *